(12) United States Patent
Whiteside et al.

(10) Patent No.: US 10,639,172 B2
(45) Date of Patent: May 5, 2020

(54) ABOVE THE KNEE POST-OPERATIVE RESIDUAL LIMB SUPPORT

(71) Applicant: Hanger, Inc., Austin, TX (US)

(72) Inventors: Stacey A. Whiteside, Chandler, AZ (US); Stephen D. Miller, Midway, GA (US)

(73) Assignee: Hanger, Inc., Austin, TX (US)

( * ) Notice: Subject to any disclaimer, the term of this patent is extended or adjusted under 35 U.S.C. 154(b) by 80 days.

(21) Appl. No.: 15/857,513

(22) Filed: Dec. 28, 2017

(65) Prior Publication Data

US 2018/0185175 A1 Jul. 5, 2018

Related U.S. Application Data

(60) Provisional application No. 62/440,204, filed on Dec. 29, 2016.

(51) Int. Cl.
| | | |
|---|---|---|
| *A61F 2/78* | (2006.01) |
| *A61F 2/76* | (2006.01) |
| *A61F 2/60* | (2006.01) |
| *A61F 2/50* | (2006.01) |
| *A61F 2/30* | (2006.01) |

(52) U.S. Cl.
CPC .............. *A61F 2/78* (2013.01); *A61F 2/60* (2013.01); *A61F 2/76* (2013.01); *A61F 2002/30441* (2013.01); *A61F 2002/5026* (2013.01); *A61F 2002/5081* (2013.01); *A61F 2002/7862* (2013.01)

(58) Field of Classification Search
CPC ....... A61F 2/78; A61F 2/80; A61F 2002/7862
See application file for complete search history.

(56) References Cited

U.S. PATENT DOCUMENTS

| | | | |
|---|---|---|---|
| 2013/0338794 A1* | 12/2013 | Whiteside ................. | A61F 2/80 623/36 |
| 2014/0371646 A1* | 12/2014 | Kozersky ................ | A61F 5/026 602/19 |
| 2018/0021153 A1 | 1/2018 | Hurley et al. | |
| 2018/0185175 A1* | 7/2018 | Whiteside ................ | A61F 2/78 |

* cited by examiner

*Primary Examiner* — Bruce E Snow
(74) *Attorney, Agent, or Firm* — Foley & Lardner LLP

(57) ABSTRACT

An above-the-knee post-operative residual limb support device is described. The support device may be used shortly after amputation of a portion of a limb, such as a portion of a patient's leg (e.g., such as in an above-the knee ("AK") amputation procedure). Such a support device may be referred to as an Immediate Post-Operative Prosthesis ("IPOP").

18 Claims, 14 Drawing Sheets

ABOVE THE KNEE POST-OPERATIVE RESIDUAL LIMB SUPPORT

CROSS-REFERENCE TO RELATED PATENT APPLICATIONS

This application claims the benefit of and priority to U.S. Provisional Patent Application No. 62/440,204, filed Dec. 29, 2016, the contents of which are incorporated herein by reference in its entirety.

BACKGROUND

The present disclosure relates generally to the field of post-operative residual limb supports and, more specifically, to post-operative residual limb supports that may provide improved fit, protection, added comfort, and function for users having above-the-knee amputations.

SUMMARY

One example embodiment relates to an above-the-knee post-operative residual limb support assembly. The support assembly includes a frame assembly comprising an upper frame and a lower frame. The upper frame is configured to extend about at least a portion of a residual limb of a wearer. The lower frame is configured to receive an end of the residual limb. The lower frame is coupled to the upper frame through a sliding connection such that upper frame and the lower frame are adjustable relative to one another in a linear manner. The support assembly further includes a liner configured to be positioned between the frame assembly and the residual limb. The liner is configured to receive a distal end of the residual limb in a central compartment of the liner. The liner comprises a base material having an open top end and a closed distal end. The closed distal end has a dome shape.

Another example embodiment relates to a frame assembly configured to extend about at least a portion of a residual limb of a wearer. The frame assembly includes an upper frame having a first slot and a lower frame having a second slot. The frame assembly further includes a first fastener extending through the first slot and the second slot, thereby coupling the upper frame to the lower frame. The first fastener is adjustable such that the first fastener can be loosened to allow the upper frame and the lower frame to slide with respect to each other and tightened to secure the upper frame and the lower frame in place with respect to each other.

These and other features, together with the organization and manner of operation thereof, will become apparent from the following detailed description when taken in conjunction with the accompanying drawings, wherein like elements have like numerals throughout the several drawings described below.

DETAILED DESCRIPTION

Referring to the figures generally, a post-operative residual limb support is described. The post-operative residual limb support may be used shortly after amputation of a portion of a limb, such as a portion of a patient's leg (e.g., such as in an above-the knee ("AK") amputation procedure). Such a support device may be referred to as an Immediate Post-Operative Prosthesis ("IPOP"). After the amputation procedure, there is typically a period of time prior to the patient being fitted with a permanent prosthesis. During this time, it is desirable to provide proper support and protection to the patient's residual limb so as to protect the patient from injury, to permit the residual limb to heal properly, and to prepare the residual limb for a permanent prosthesis. If not properly supported and protected, the residual limb may swell and/or take on undesirable shapes. Further, patients sometimes fall after forgetting that a limb has been amputated and that they are now missing a portion of their leg. A lack of support and/or protection for the residual limb may result in other undesirable events. As such, various embodiments disclosed herein are directed to providing an improved post-operative residual limb support assembly intended to provide proper support and protection for residual limbs after AK amputation procedures.

Figure 1:
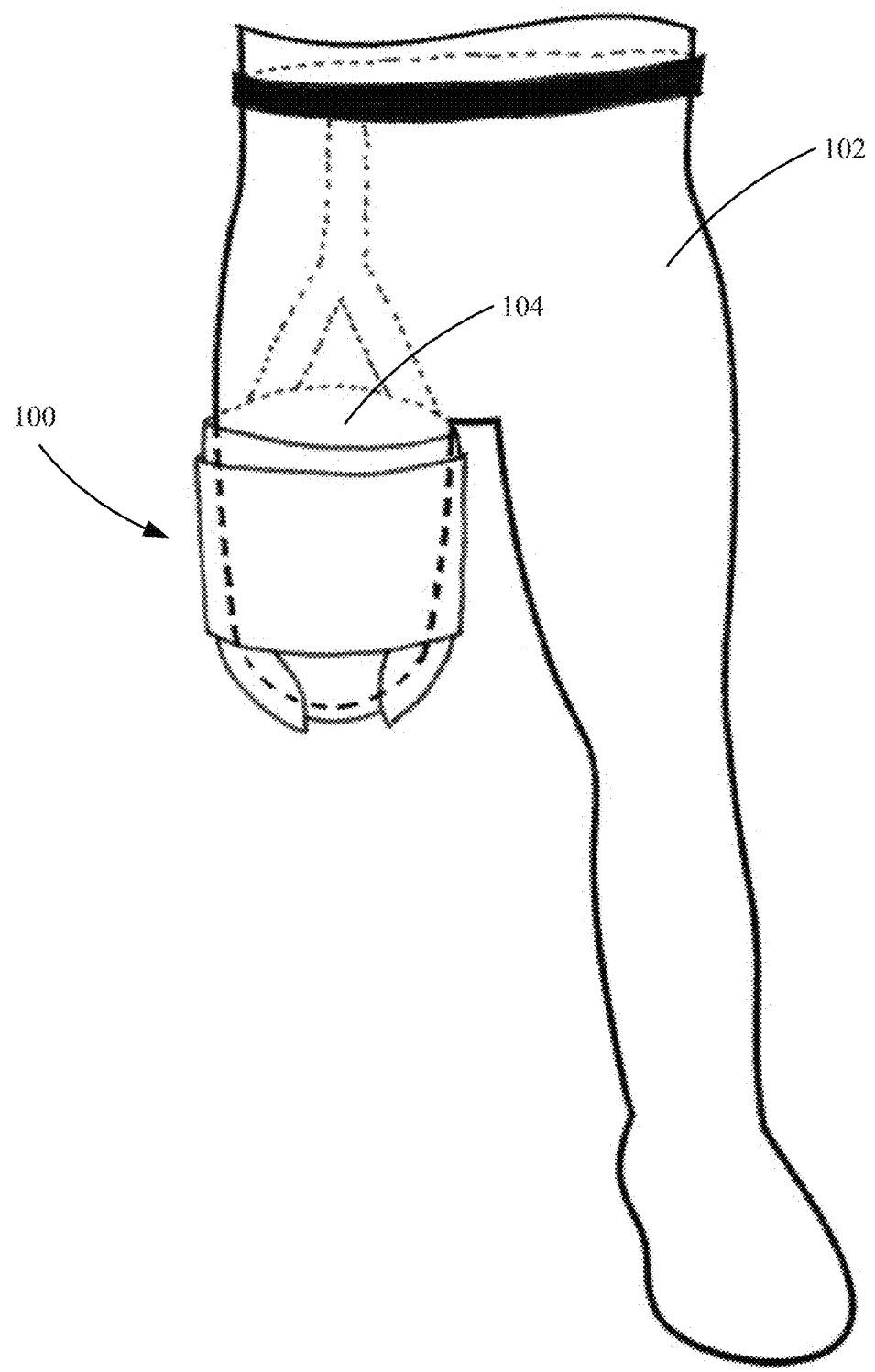
FIG. 1 is a view of a post-operative residual limb support device fitted on a patient, according to an example embodiment.

Referring to FIG. 1, a view of a post-operative residual limb support device 100 fitted on a patient 102 (a user or wearer of the support device 100) is shown, according to an example embodiment. As shown in FIG. 1, the patient 102 is missing a lower portion of one of the patient's legs. The lower portion of the leg may have been removed, for example, during an AK amputation procedure. Accordingly, the patient 102 has a residual limb 104. In some arrangements, the residual limb 104 does not include a knee joint. As described below in further detail with respect to FIGS. 2 through 13, the support device 100 is an IPOP device that is configured to support and protect the residual limb 104.

Figure 2:
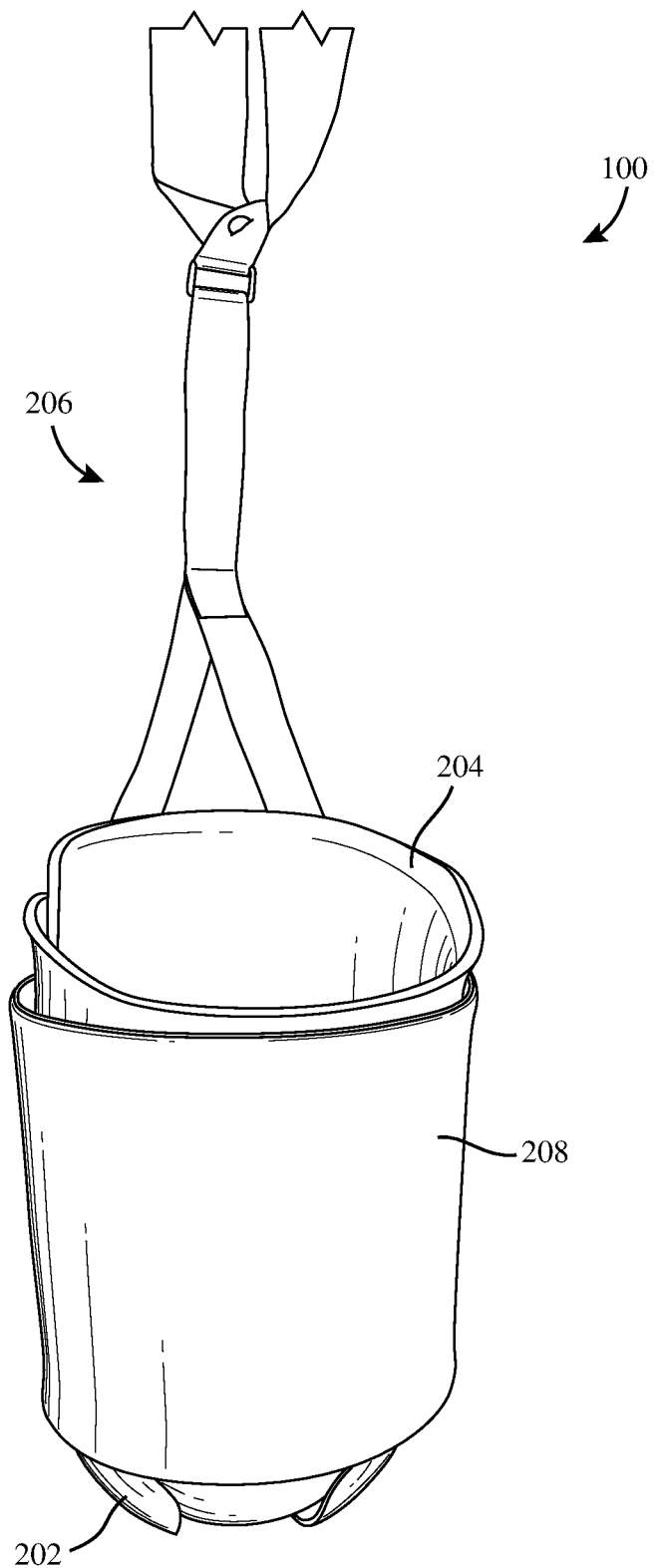
FIG. 2 is a front perspective view of the post-operative residual limb support device of FIG. 1.
Figure 3:
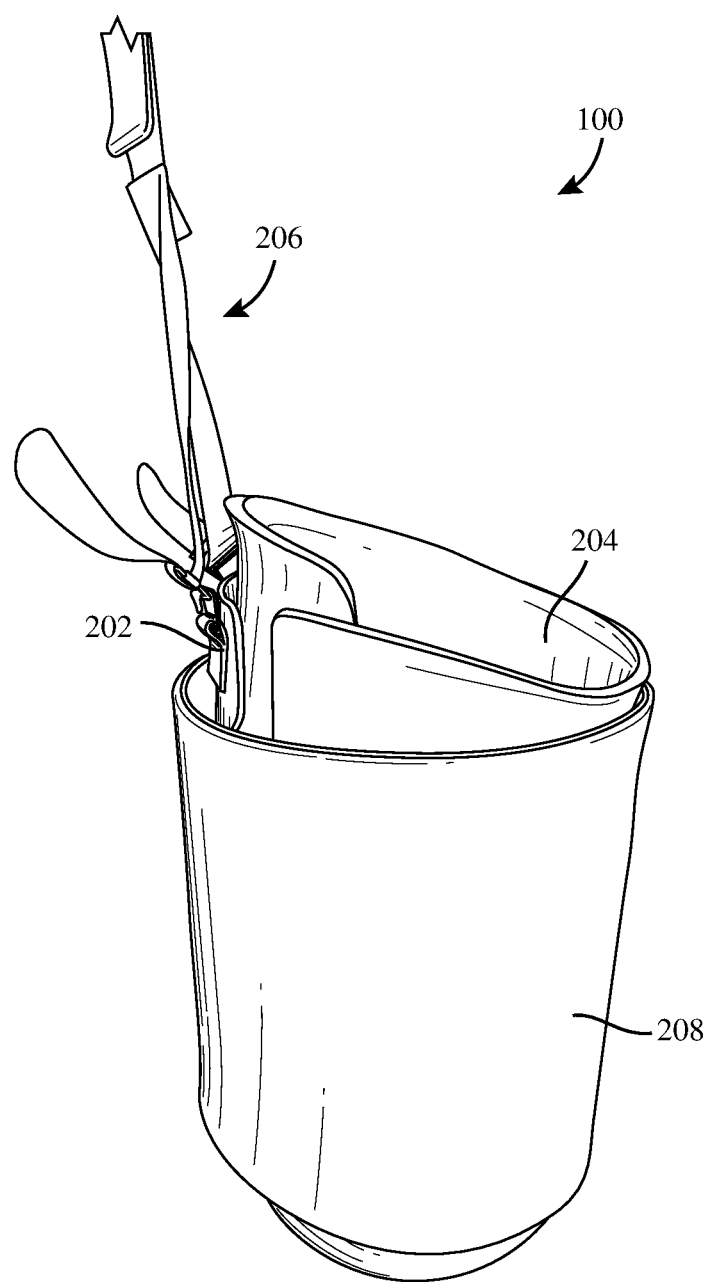
FIG. 3 is a side perspective view of the post-operative residual limb support device of FIG. 1.

Referring to FIG. 2, a front perspective view of the post-operative residual limb support device 100 is shown. Referring to FIG. 3, a side perspective view of the post-operative residual limb support device 100 is shown. The support device 100 includes four basic components: a frame assembly 202, an inner liner 204, a suspension assembly 206, and an outer wrap 208. Each of the components of the support device 100 are described in further detail below with respect to FIGS. 4 through 12.

Figure 4:
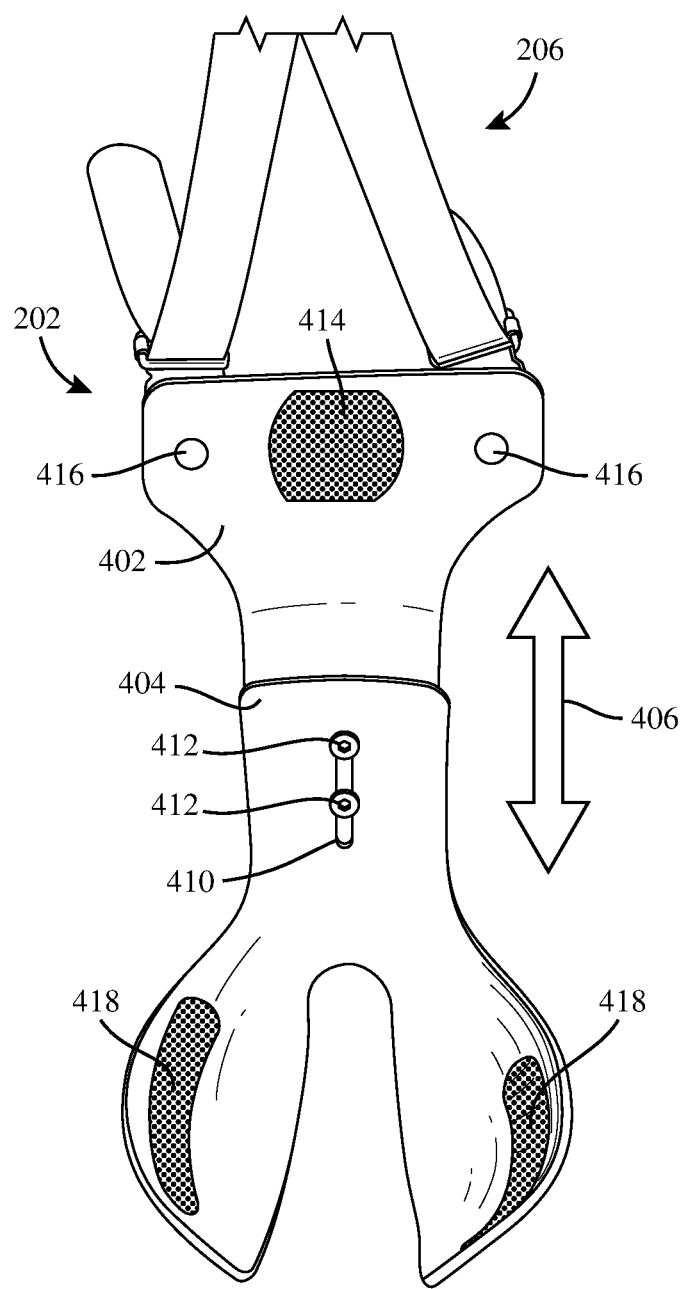
FIG. 4 shows a front perspective view of a frame assembly of the post-operative residual limb support device of FIG. 1, according to an example embodiment.
Figure 5:
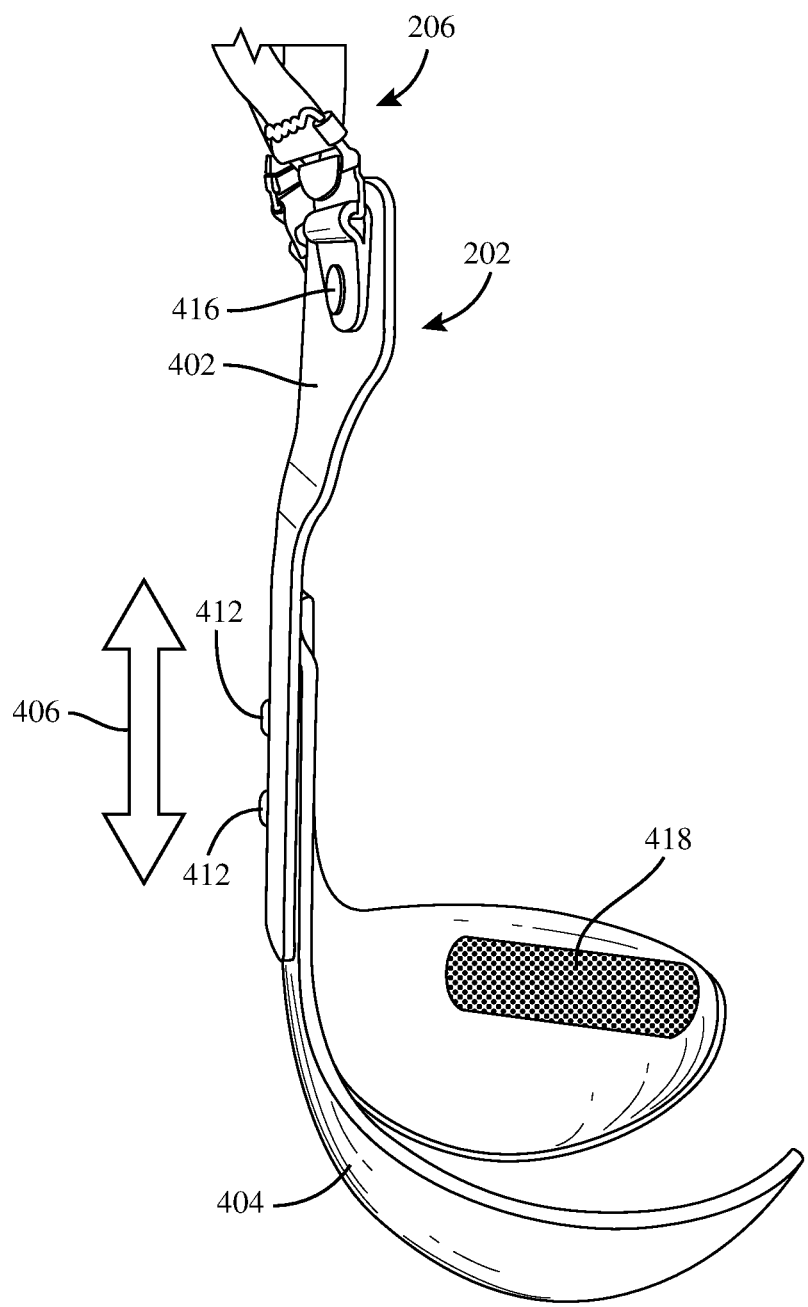
FIG. 5 shows a side perspective view of the frame assembly of FIG. 4.
Figure 6:
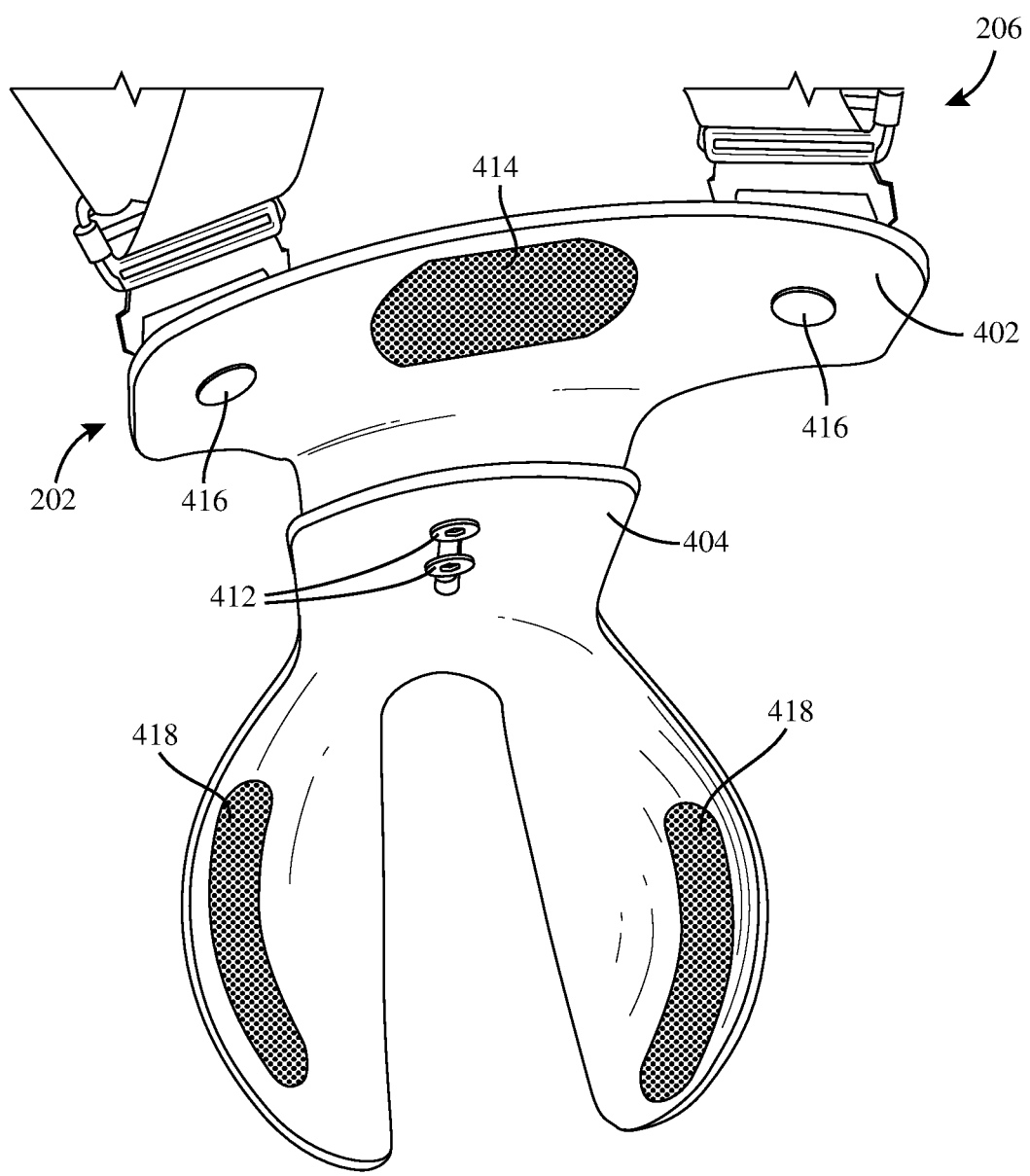
FIG. 6 shows a top perspective view of the frame assembly of FIG. 4.
Figure 7B:
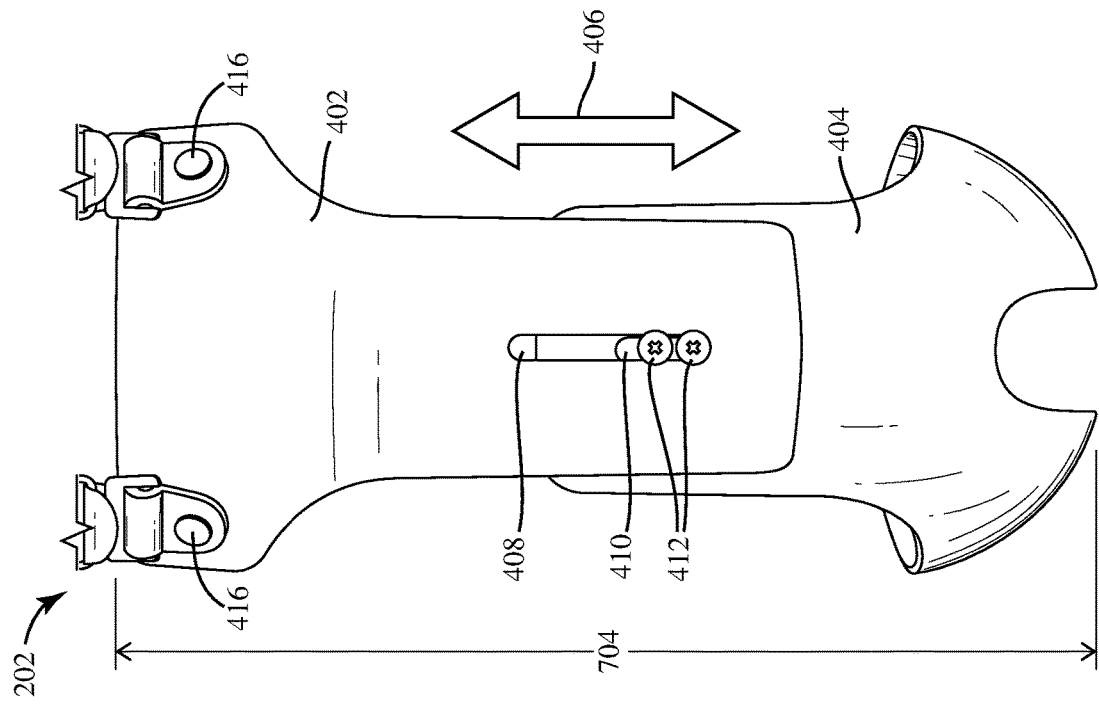
FIG. 7B shows a back perspective view of the frame assembly of FIG. 4 in an extended position.
Figure 7A:
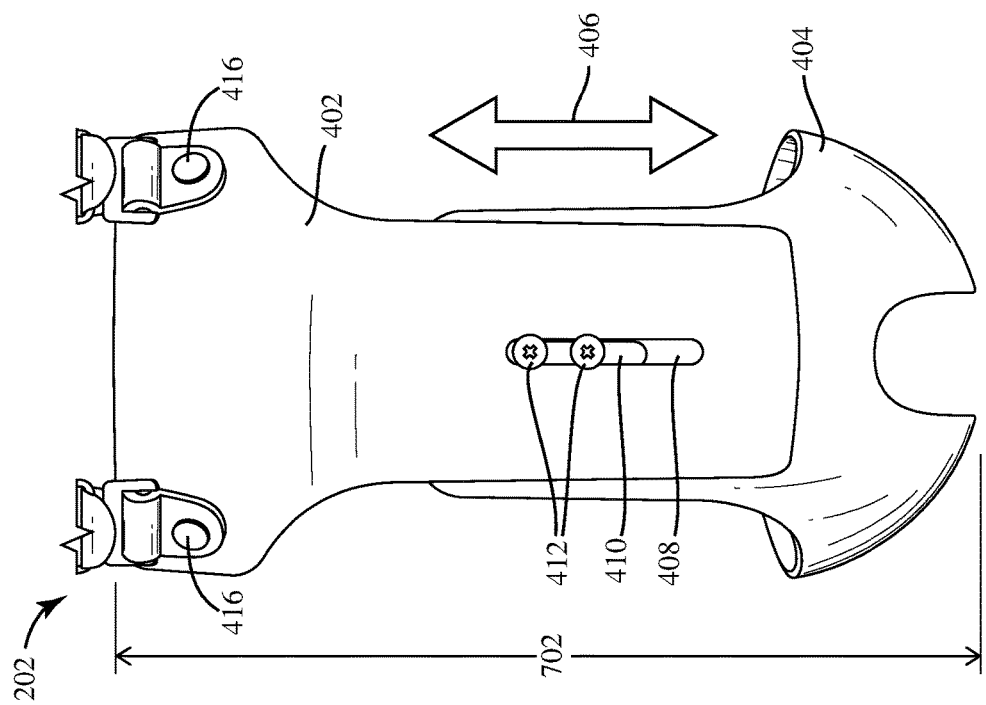
FIG. 7A shows a back perspective view of the frame assembly of FIG. 4 in a retracted position.

Referring to FIGS. 4-6, 7A, and 7B, different perspective views of the frame assembly 202 are shown. FIG. 4 shows a front perspective view of the frame assembly 202. FIG. 5 shows a side perspective view of the frame assembly 202. FIG. 6 shows a top perspective view of the frame assembly 202. FIG. 7A shows a back perspective view of the frame assembly 202 in a retracted position. FIG. 7B shows a back perspective view of the frame assembly 202 in an extended position.

The frame assembly 202 includes an upper frame 402 and a lower frame 404. The upper frame 402 is configured to extend about at least a portion of the residual limb 104 (e.g., as shown in FIG. 1), and the lower frame 404 is configured to receive a distal end of the inner liner 204 and a distal end of the residual limb 104 (e.g., as shown in FIG. 1). The upper frame 402 and the lower frame 404 are constructed of a rigid material, such as a moldable plastic (e.g., polyvinyl chloride, acrylic, acrylic-polyvinyl chloride, acrylonitrile butadiene styrene, polypropylene, a homo-polymer, etc.), metal (e.g., aluminum, steel, stainless steel, titanium, etc.), three-dimensional printable material (e.g., plastics, metals, etc.), thermosetting plastics or polymers (e.g., epoxy, polyester fiberglass, polyurethane, polyimides, melamine resin, etc.), or the like. The upper frame 402 and the lower frame 404 are coupled to each other and adjustable with respect to each other in a sliding, linear manner along a sliding axis 406 (as described in further detail below with respect to FIGS. 7A and 7B). To facilitate the sliding coupling, the upper frame 402 and the lower frame 404 are coupled via a sliding connection. The upper frame 402 includes a first slot 408, and the lower frame 404 includes a second slot 410 (shown best in FIGS. 7A and 7B). Two adjustable fasteners 412 extend through the first slot 408 and the second slot 410, thereby connecting the upper frame 402 and the lower frame 404. The sliding connection is defined by the first slot 408, the second slot 410, and at least one of the two adjustable fasteners 412. The adjustable fasteners 412 may each include, for example, a threaded screw or bolt extending through the first slot 408 and the second slot 410, and a threaded nut attached to the threaded screw or bolt. Accordingly, the adjustable fasteners 412 can be loosened to allow the upper frame 402 and the lower frame 404 to slide with respect to each other and tightened to secure the upper frame 402 and the lower frame 404 into position (e.g., as described in further detail below with respect to FIGS. 7A and 7B). The use of two adjustable fasteners 412 instead of one fastener also helps to keep the upper frame 402 and the lower frame 404 axially aligned with respect to the sliding axis 406. In an alternate arrangement, the upper frame 402 and the lower frame 404 are replaced with a singular frame member of a fixed length if no adjustability of the length of the frame assembly 202 is desired by the patient 102.

The upper frame 402 is substantially T-shaped. Accordingly, the upper portion of the upper frame 402 is wider than the lower portion of the upper frame 402 with respect to the sliding axis 406. The lower portion of the upper frame 402 includes the first slot 408. The upper portion of the upper frame 402 includes a first liner coupler 414. As described in further detail below with respect to FIGS. 10 and 11, the first liner coupler 414 is configured to interact with a mating coupler on the inner liner 204 to secure the inner liner 204 to the upper frame 402. The first liner coupler 414 may be, for example, an adhesive pad, a first half of a hook-and-loop coupler (e.g., Velcro®), a first half of a snap, or the like. Additionally, the upper portion of the upper frame 402 includes fasteners 416 that are used to secure the suspension assembly 206 to the upper frame 402. The fasteners 416 may include snaps, rivets, or the like. The positioning of the fasteners 416 may differ from the positioning shown in the figures to account for abnormalities in the shape of the residual limb 104, the condition of the residual limb 104, and/or ease of use by the patient 102.

The lower frame 404 has a substantially inverted Y-shape. Accordingly, the upper portion of the lower frame 404 is narrower than the lower portion of the lower frame 404 with respect to the sliding axis 406. The upper portion of the lower frame 404 is approximately the same width as the lower portion of the upper frame 402. The upper portion of the lower frame 404 includes the second slot 410. The lower portion of the lower frame 404 is bent to form a bowl shape (as shown best in FIG. 5). The bowl shape of the lower frame 404 is configured to receive the distal end of the inner liner 204 and the distal end of the residual limb 104 of the patient 102. Similar to the upper portion of the upper frame 402, the lower portion of the lower frame 404 includes pair of second liner couplers 418. As described in further detail below with respect to FIGS. 10 and 11, the second liner couplers 418 are configured to interact with mating couplers on the distal end of the inner liner 204 to secure the inner liner 204 to the lower frame 404. The second liner couplers 418 may be, for example, adhesive pads, first halves of a hook-and-loop couplers (e.g., Velcro®), first halves of a snaps, or the like.

Referring to FIGS. 7A and 7B, the adjustability of the frame assembly 202 is shown. As shown in FIG. 7A, the frame assembly 202 is in a retracted position. As shown in FIG. 7B, the frame assembly 202 is in an extended position. As described above, the sliding coupling between the upper frame 402 and the lower frame 404 facilitates the adjustment of the frame assembly 202 to any length between the retracted position and the extended position. In the retracted position, the frame assembly 202 has a first axial height 702. In the extended position, the frame assembly has a second axial height 704. The second axial height 704 is larger than the first axial height 702. The adjustability of the frame assembly 202 allows the support device 100 to be used with different sized patients, patients having different amputation locations, and patients with different physical characteristics (e.g., different sized legs).

Figure 8:
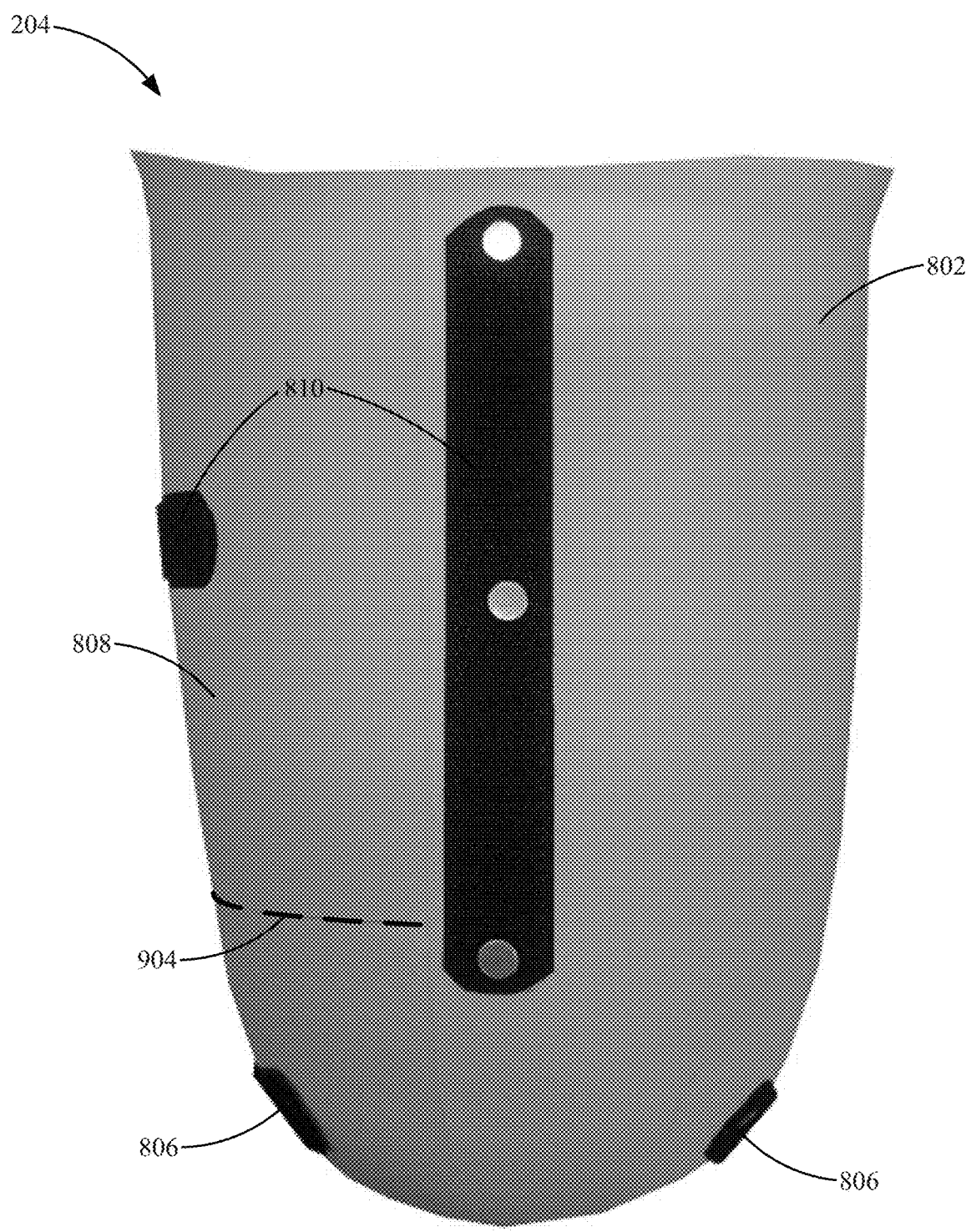
FIG. 8 shows a front view of an inner liner of the post-operative residual limb support device of FIG. 1, according to an example embodiment.
Figure 9:
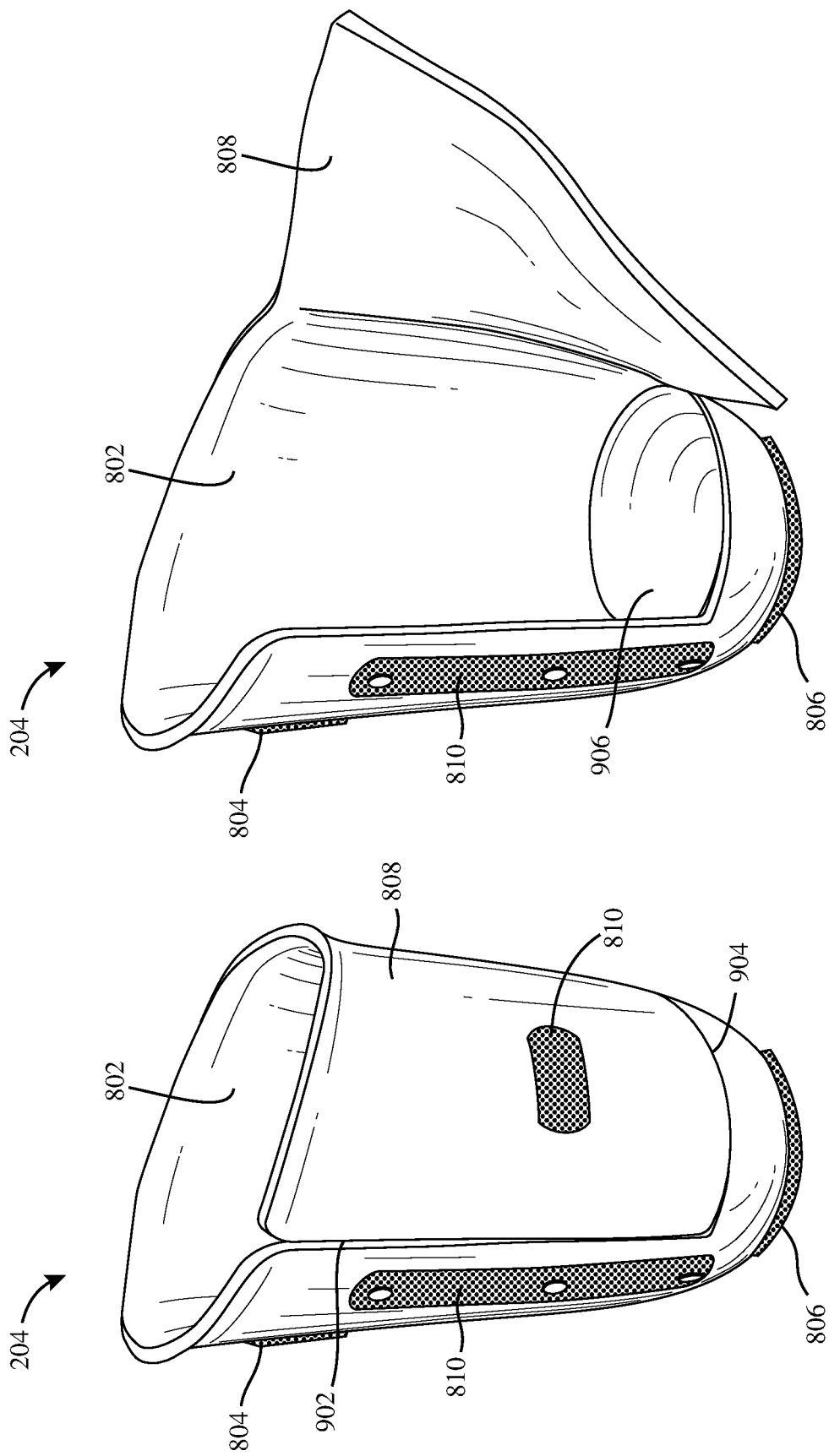
FIG. 9A shows a perspective view of the inner liner of FIG. 8 having a flap portion closed.
FIG. 9B shows a perspective view of the liner of FIG. 8 having the flap portion open.
FIG. 9C shows a block diagram of a heating circuit of the inner liner of FIG. 8.

Referring to FIGS. 8, 9A, and 9B, views of the inner liner 204 are shown. FIG. 8 shows a front view of the inner liner 204. FIG. 9A shows a perspective view of the inner liner 204 having the flap portion 808 closed. FIG. 9B shows a perspective view of the inner liner 204 having the flap portion 808 open.

The inner liner 204 is configured to be positioned between the frame assembly 202 and the residual limb 104 of the patient 102. The inner liner 204 is configured to receive and at least partially surround the residual limb 104 of the patient 102. The inner liner 204 comprises a base 802 that is constructed of a material that is more flexible (less rigid) than the frame assembly 202. For example, the inner liner 204 may be constructed out of any formable foam, plastic or rubber materials, such as ethylene-vinyl acetate foam, thermoplastic closed-cell foam, polyethylene foam, polyethylene, 3D printable material, thermoset foams, thermo-formable foams, memory foam, closed-cell foam, open-cell foam, or the like. As shown in the figures, the inner liner 204 is shaped as a cylinder that has an open top end and a bottom end that is closed and has a dome shape. Accordingly, the base 802 defines a central compartment that receives the residual limb 104 (e.g., as shown in FIG. 1).

The inner liner 204 includes a first frame coupler 804 (shown in FIG. 9A). The first frame coupler 804 is positioned and configured to interact with the first liner coupler 414 of the frame assembly 202 to removably secure the inner liner 204 to the upper frame 402. Accordingly, the first frame coupler 804 may be, for example, an adhesive pad, a second half of a hook-and-loop coupler (e.g., Velcro®), a second half of a snap, or the like. The first frame coupler 804 may be secured to the base 802 through adhesive, rivets, or the like.

The inner liner 204 includes a pair of second frame couplers 806. The second frame couplers 806 are positioned on the bottom end (dome portion) of the base 802. The second frame couplers 806 are positioned and configured to interact with the pair of second liner couplers 418 of the frame assembly 202 to removably secure the inner liner 204 to the lower frame 404. Accordingly, the second frame couplers 806 may be, for example, adhesive pads, second halves of a hook-and-loop coupler (e.g., Velcro®), second halves of snaps, or the like. The second frame couplers 806 may be secured to the base 802 through adhesive, rivets, or the like.

As shown best in FIGS. 9A and 9B, the base 802 of the inner liner 204 includes a flap portion 808. The flap portion 808 is created by a vertical axial cut 902 and a horizontal circumferential cut 904 in the base 802 (shown as dashed lines in FIGS. 8 and 9A). The cuts 902 and 904 that define the flap portion 808 allow the flap portion 808 to be movable between a closed position (e.g., as shown in FIG. 9A) and an open position that is bent away from the base 802 (e.g., as shown in FIG. 9B). When the flap portion 808 is in the open position, the patient 102 can easily insert the residual limb 104 into the inner liner 204 with less strain and pain than if the flap portion 808 did not exist.

The inner liner 204 includes a plurality of wrap fasteners 810. In some arrangements, the inner liner 204 includes three wrap fasteners 810. In other arrangements, the inner liner 204 includes more or less than three wrap fasteners 810. As described in further detail below with respect to FIG. 13, the wrap fasteners 810 are configured to grip the outer wrap 208. When the outer wrap 208 is gripped by the wrap fasteners 810, the outer wrap 208 secures the flap portion 808 in the closed position (shown in FIG. 9A). In some arrangements, the wrap fasteners 810 are hook-and-loop couplers (e.g., Velcro®) or the like. The wrap fasteners 810 may be secured to the base 802 through adhesive, rivets, or the like.

As shown in FIG. 9B, in some arrangements, the inner liner 204 is fitted with a support pad 906. The support pad 906 is removably received at a bottom end of the central compartment. The support pad 906 may be constructed of a foam that is more flexible (i.e., less rigid) than the material forming the base 802. In some arrangements, the support pad 906 is formed from a foam, such as plastic or rubber foams, ethylene-vinyl acetate foam, thermoplastic closed-cell foam, polyethylene foam, polyethylene, 3D printable material, thermoset foams, thermos-formable foams, memory foam, closed-cell foam, open-cell foam, or the like. For example, the support pad 906 may be formed from a memory foam. The support pad 906 provides additional support to the distal end of the residual limb 104 when the residual limb 104 is received in the central compartment of the inner liner 204.

In some arrangements, heat can be applied to the inner liner 204. The heat can be used for therapeutic purposes (e.g., to heat a portion of the residual limb 104) or to reshape, enlarge, or shrink the inner liner 204 (or the central compartment formed by the inner liner 204). For example, as shown in FIG. 9C, in some arrangements, the inner liner 204 includes at least one heating element 908 and a control device 910, which can be activated to apply heat to the inner liner 204, for example, to shrink or enlarge the central compartment to account for reduced swelling of the residual limb 104 over time. In such an arrangement, the heating elements 908 can be positioned at various positions along the inner liner 204 (e.g., in an array) and may be individually (independent of one another) activated by the control device 910 so as to allow the control device 910 to selectively reshape targeted portions of the inner liner 204 or to selectively target portions of the residual limb 104 for heating. The heating elements 908 may be embedded within the material of the inner liner 204 or positioned on an external surface and/or internal surface of the inner liner 204. In some arrangements, the control device 910 can receive feedback from at least one temperature sensor 912 to aid in maintaining the appropriate temperature depending on whether the inner liner 204 needs to be reshaped, enlarged, or shrunk or depending on the type of heat treatment being applied to the residual limb 104.

The control device 910 may include, for example, a processor and memory having programming instructions that, when executed by the processor, control the operation of the control device 910 and the heating elements 908. The control device 910 also includes a user input (e.g., to receive heating instructions from a technician or a technician device, to receive residual limb 104 heating instructions, etc.). For example, if the central compartment becomes too large for the residual limb 104 because of reduced swelling, the heating element 908 of the inner liner 204 can be activated, which causes the inner liner 204 to slightly shrink, thereby reducing the size of the central compartment. Additionally, the heat applied by the heating element 908 allows the shape of the inner liner 204 (and thus the central compartment) to be adjusted as needed. In some arrangements, the inner liner 204 is configured to receive foam shims that alter the shape of the central compartment (e.g., to account for swelling changes of the residual limb 104). In other arrangements, a technician can selectively apply heat from an external source (e.g., from a heat gun, from a blow dryer, etc.) to shrink or enlarge the central compartment to account for reduced swelling of the residual limb 104 over time. In further arrangements, the inner liner 204 is insulated or has insulating characteristics to retain warmth and/or to be used for hot and/or cold compresses of the residual limb 104.

Figure 10:
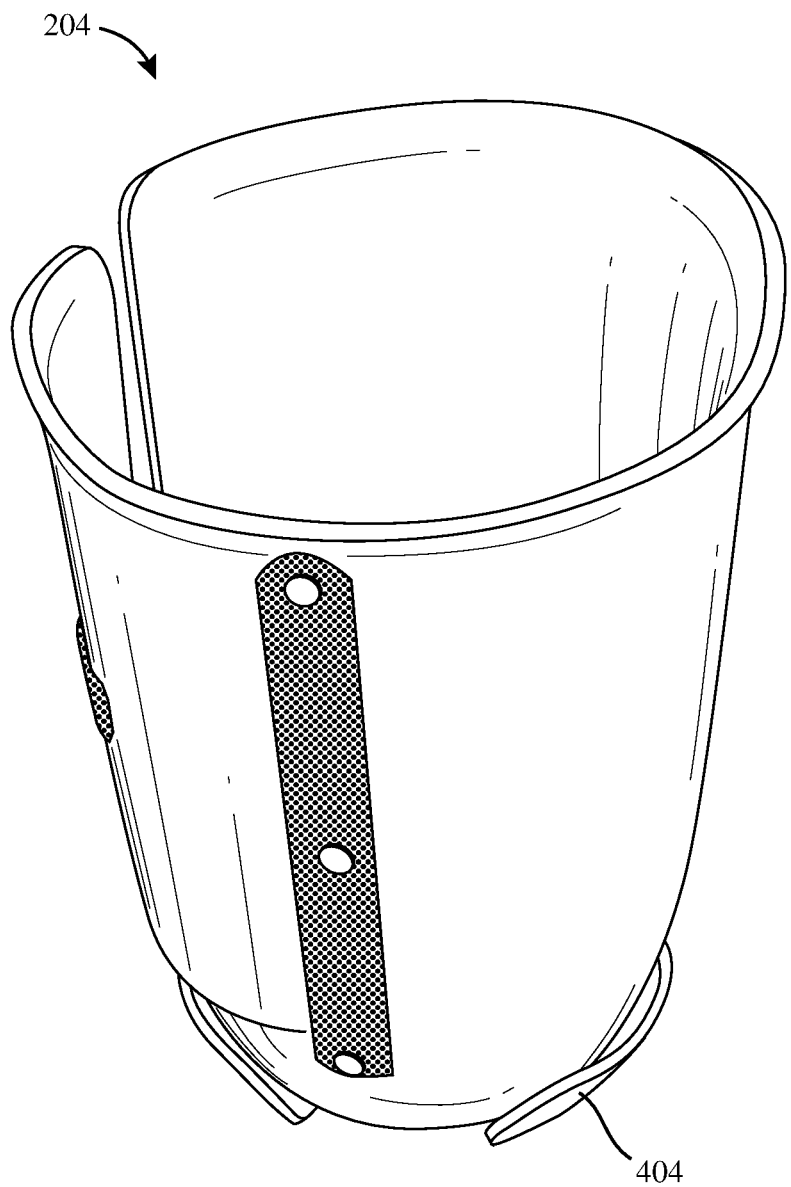
FIG. 10 and FIG. 11 each show a different perspective view of the inner line of FIG. 8 installed in the frame assembly of FIG. 4.
Figure 11:

Referring to FIGS. 10 and 11, two different perspective views of the inner liner 204 installed in the frame assembly 202 are shown. As shown in FIGS. 10 and 11, the bottom end (the dome portion) of the inner liner 204 is received in the bowl shaped portion of the lower frame 404. The upper frame 402 supports the circumferential surface of the inner liner 204. When the inner liner 204 is installed in the frame assembly 202, the first frame coupler 804 connects to the first liner coupler 414, and the pair of second frame couplers 806 connect to the pair of second liner couplers 418 to removably secure the inner liner 204 to the frame assembly 202.

Figure 12:
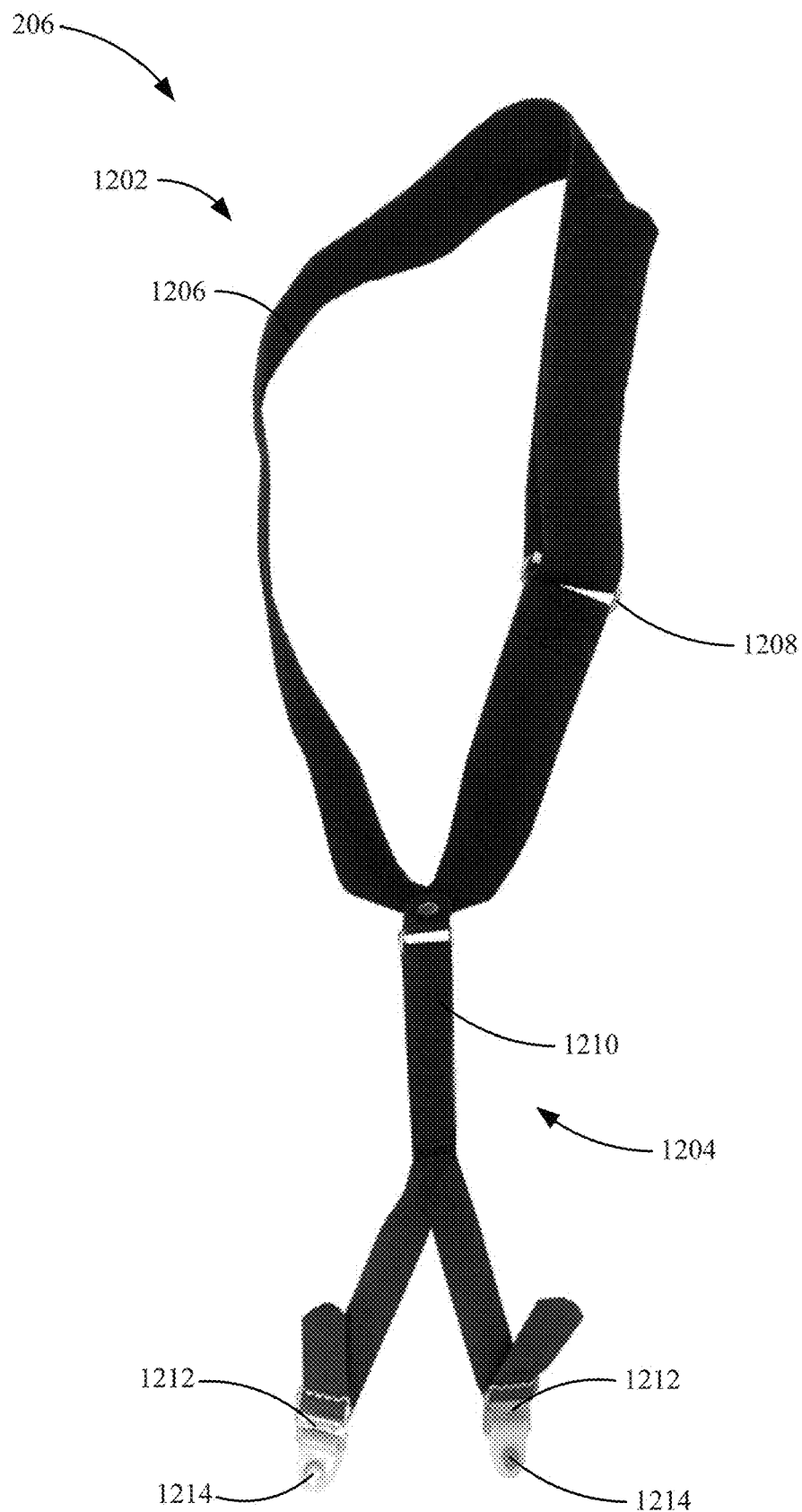
FIG. 12 shows a view of a suspension assembly of the post-operative residual limb support device of FIG. 1, according to an example embodiment.

Referring to FIG. 12, a view of the suspension assembly 206 is shown, according to an example embodiment. Generally, the suspension assembly 206 is configured to support the post-operative residual limb support device 100 in substantially the same position on the patient 102 such that the support device 100 does not fall off of the residual limb 104. The suspension assembly 206 comprises a waist belt 1202 and a vertical support 1204. The waist belt 1202 is configured to wrap around a waist of the patient 102. The waist belt 1202 comprises a strap 1206 that forms a loop. In some arrangements, the strap 1206 is formed of nylon. The circumference of the loop is adjustable through a tri-glide bracket 1208. In some embodiments, the tri-glide bracket 1208 is a strap adjuster. For example, the tri-glide bracket 1208 may be a strap adjuster, such as a buckle or slide comprising an oblong ring with a crossbar extending therethrough. The strap 1206 of the waist belt 1202 is coupled to a strap 1210 of the vertical support 1204. The vertical support 1204 has an overall Y-shape. The branched portion of the Y-shaped strap 1210 includes a pair of tri-glide brackets 1212 such that the overall length of the vertical support 1204 is adjustable. Each of the tri-glide brackets 1212 is coupled to a frame fastener 1214. Each frame fastener 1214 is structured to connect the suspension assembly 206 to the upper frame 402 of the frame assembly 202 (e.g., as shown in FIG. 5). In some arrangements, the frame fasteners 1214 are positioned laterally so as to be attached to a lateral side of the upper frame 402, which allows for easier user access to the frame fasteners 1214. In such arrangements, the upper frame 402 and the lower frame 404 may be offset laterally to account for the different positioning of the frame fasteners 1214. The frame fasteners 1214 may rotatably connect the suspension assembly 206 to the upper frame 402. The frame fasteners 1214 may be snaps, rivets, or the like.

Figure 13:
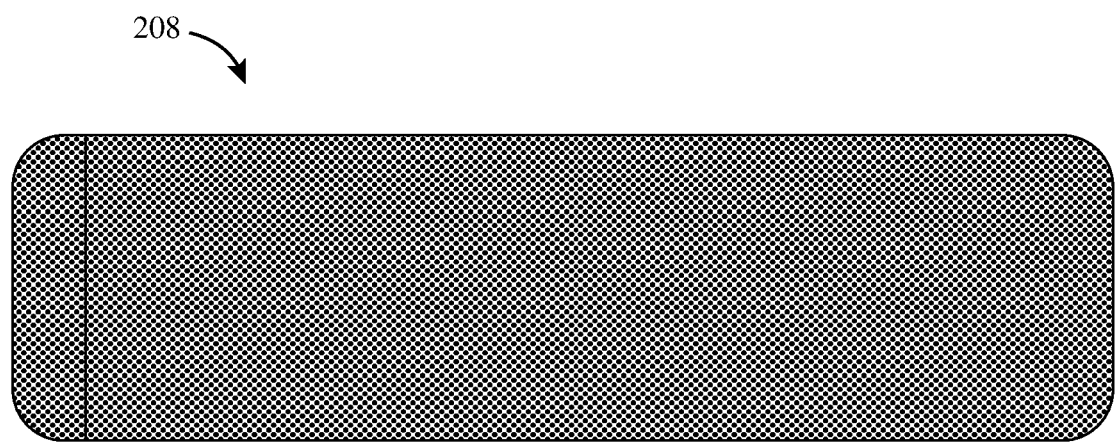
FIG. 13 shows a front view of the outer wrap of the post-operative residual limb support device of FIG. 1, according to an example embodiment.

Referring to FIG. 13, a front view of the outer wrap 208 is shown, according to an example embodiment. Generally, the outer wrap 208 is a flexible band that has an elastic characteristic such that the outer wrap 208 can stretch when force is applied and return to shape when the force is removed. The outer wrap 208 has a front side (shown in FIG. 13) and a back side (not shown). The back side of the outer wrap 208 includes a fastener material (e.g., a hook-and-loop coupler such as Velcro®). The front side of the outer wrap 208 is generally free of the fastener material. However, the front side includes a narrow band of the fastener material 1302 such that when the outer wrap 208 is wrapped around an object and the back side overlaps with the narrow band of the fastener material 1302, the outer wrap 208 secures itself in place through interaction between the narrow band of the fastener material 1302 and the back side of the outer wrap 208. Additionally, when the outer wrap 208 is wrapped around the inner liner 204 and the frame assembly 202 such that the back side of the outer wrap 208 is facing the inner liner 204 and the frame assembly 202, the fastener material on the back side of the outer wrap 208 grips the wrap fasteners 810 of the inner liner 204 to secure the flap portion 808 of the inner liner 204 in the closed position (e.g., as shown in FIGS. 2 and 3).

Figure 14:
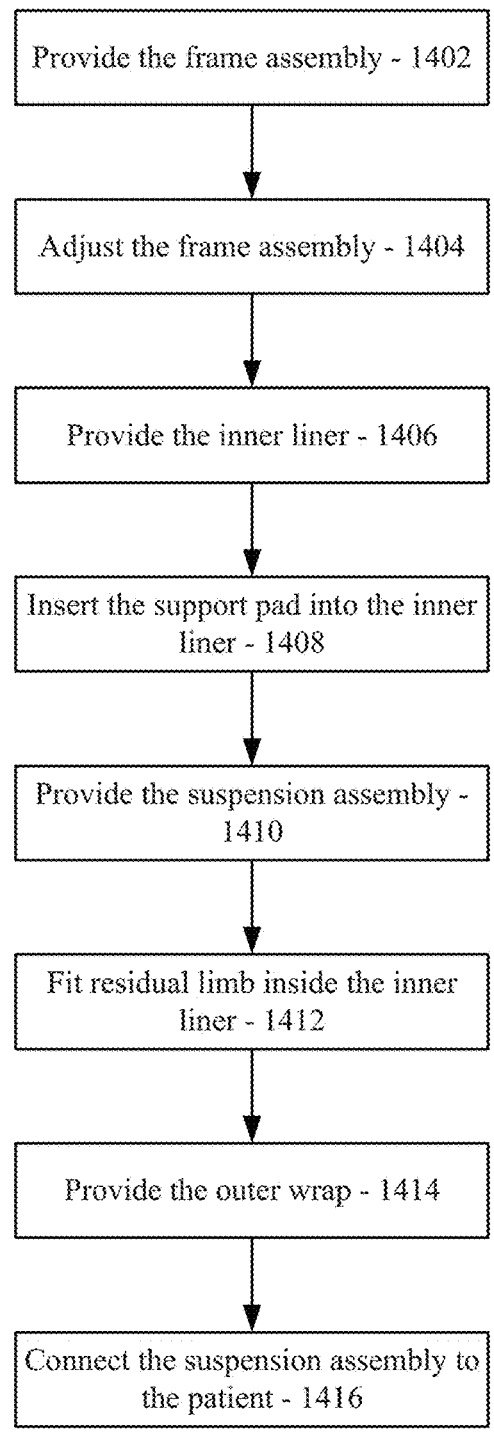
FIG. 14 shows a flow diagram of a method of assembling the post-operative residual limb support device of FIG. 1 and fitting the device to a patient, according to an exemplary embodiment.

Referring to FIG. 14, a flow diagram of a method 1400 of assembling the post-operative residual limb support device 100 and fitting the support device 100 to the patient 102 is shown, according to an exemplary embodiment. The method 1400 begins at 1402 when the frame assembly 202 is provided. The frame assembly 202 includes the upper frame 402 and the lower frame 404 as described above with respect to FIGS. 4-6, 7A, and 7B. At 1404, the frame assembly 202 is adjusted. As described above with respect to FIGS. 7A and 7B, the length of the frame assembly 202 can be adjusted depending on the characteristics of the patient 102 and the residual limb 104. The upper frame 402 can be extended or retracted with respect to the lower frame 404 to change the length. At 1406, the inner liner 204 is provided. The inner liner 204 is connected to the frame assembly 202 by connecting the first frame coupler 804 to the first liner coupler 414, and by connecting the pair of second frame couplers 806 to the pair of second liner couplers 418. At 1408, the support pad 906 is inserted into the inner liner 204. The support pad 906 is inserted into a bottom end of the central compartment of the inner liner 204. At 1410, the suspension assembly 206 is provided. The suspension assembly 206 is connected to the upper frame 402 of the frame assembly 202 via the frame fasteners 1214.

At 1412, the residual limb 104 is inserted into the inner liner 204. The flap portion 808 of the inner liner 204 is opened to allow the residual limb 104 to fit into the central compartment of the inner liner 204. Once the residual limb 104 is fully received and properly positioned within the central compartment of the inner liner 204, the flap portion 808 is closed. At 1414, the outer wrap 208 is provided. The outer wrap 208 wraps around the inner liner 204 and the frame assembly 202 thereby securing the flap portion 808 in the closed position (e.g., as shown in FIG. 9A). The outer wrap 208 is held in place by the wrap fasteners 810 of the inner liner and the narrow band of the fastener material 1302 of the outer wrap 208 (e.g., as described above with respect to FIG. 13). At 1416, the suspension assembly 206 is connected to the patient 102. The vertical support 1204 of the suspension assembly 206 is adjusted such that the distance between the frame assembly 202 and the waist belt 1202 is appropriate for the waist belt 1202 to wrap around the waist of the patient 102. The waist belt 1202 is wrapped around the waist of the patient 102 and tightened in place (e.g., as shown in FIG. 1).

It should be noted that any use of the terms "example," "exemplary," or similar terms herein to describe various embodiments is intended to indicate that such embodiments are possible examples, representations, and/or illustrations of possible embodiments (and such term is not intended to connote that such embodiments are necessarily extraordinary or superlative examples).

References herein to the positions of elements (e.g., "top," "bottom," "above," "below," etc.) are merely used to describe the orientation of various elements in the figures. It should be noted that the orientation of various elements may differ according to other example embodiments, and that such variations are intended to be encompassed by the present disclosure.

The terms "coupled" and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various example embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Additionally, features from particular embodiments may be combined with features from other embodiments as would be understood by one of ordinary skill in the art. Other substitutions, modifications, changes and omissions may also be made in the design, operating conditions and arrangement of the various example embodiments without departing from the scope of the present invention.

What is claimed is:

1. An above-the-knee post-operative residual limb support assembly comprising:
   a frame assembly comprising an upper frame and a lower frame, wherein the upper frame is configured to extend about at least a portion of a residual limb of a wearer, the lower frame is configured to receive an end of the residual limb, and the lower frame is coupled to the upper frame through a sliding connection such that upper frame and the lower frame are adjustable relative to one another in a linear manner;
   a liner configured to be positioned between the frame assembly and the residual limb, the liner is configured to receive a distal end of the residual limb in a central compartment of the liner, the liner comprising a base material having an open top end and a closed distal end, wherein the closed distal end has a dome shape; and
   a suspension assembly configured to support the above-the-knee post-operative residual limb support assembly on the wearer, wherein the suspension assembly comprises a waist belt and a vertical support coupled to the waist belt.

2. The above-the-knee post-operative residual limb support assembly of claim 1, wherein the sliding connection comprises a first slot in the upper frame, a second slot in the lower frame, and a fastener extending through the first slot and the second slot, the first slot and the second slot defining a sliding axis.

3. The above-the-knee post-operative residual limb support assembly of claim 2, wherein the fastener is an adjustable fastener that can be loosened to allow the upper frame and the lower frame to slide with respect to each other and tightened to secure the upper frame and the lower frame in place with respect to each other.

4. The above-the-knee post-operative residual limb support assembly of claim 1, wherein the upper frame has a substantially T-shape.

5. The above-the-knee post-operative residual limb support assembly of claim 1, wherein the lower frame has a substantially inverted Y-shape.

6. The above-the-knee post-operative residual limb support assembly of claim 1, wherein a lower portion of the lower frame forms a bowl shape configured to receive a distal end of the liner.

7. The above-the-knee post-operative residual limb support assembly of claim 1, wherein the liner is removably coupled to the frame assembly by a fastener.

8. The above-the-knee post-operative residual limb support assembly of claim 1, wherein the base material of the liner comprises a flap portion that can bend between an open position and a closed position, wherein when the flap portion is in the open position, the residual limb can be inserted into the liner.

9. The above-the-knee post-operative residual limb support assembly of claim 8, further comprising an outer wrap partially surrounding the liner and the frame assembly, the outer wrap being removably coupled to the frame assembly and the liner such that when the outer wrap is positioned on the above-the-knee post-operative residual limb support assembly, the flap portion is retained in the closed position.

10. The above-the-knee post-operative residual limb support assembly of claim 1, wherein the vertical support is coupled to the upper frame.

11. The above-the-knee post-operative residual limb support assembly of claim 10, wherein a length of the vertical support is adjustable through a tri-glide bracket.

12. A frame assembly configured to extend about at least a portion of a residual limb of a wearer, the frame assembly comprising:
    an upper frame having a first slot;
    a lower frame having a second slot; and
    a first fastener extending through the first slot and the second slot, thereby coupling the upper frame to the lower frame, wherein the first fastener is adjustable such that the first fastener can be loosened to allow the upper frame and the lower frame to slide with respect to each other and tightened to secure the upper frame and the lower frame in place with respect to each other;
    wherein the frame assembly is configured to be supported on the wearer by a suspension assembly, the suspension assembly comprising a waist belt and a vertical support coupled to the waist belt.

13. The frame assembly of claim 12, wherein the first slot and the second slot define a sliding axis, and wherein the upper frame and the lower frame can slide along the sliding axis when the fastener is loosened.

14. The frame assembly of claim 12, further comprising a second fastener extending through the first slot and the second slot.

15. The frame assembly of claim 12, wherein the first fastener includes a threaded bolt extending through the first slot and the second slot and a threaded nut attached to the threaded bolt.

16. The frame assembly of claim 12, wherein the upper frame has a substantially T-shape such that an upper portion of the upper frame is wider than a lower portion of the upper frame, wherein the lower portion of the upper frame includes the first slot.

17. The frame assembly of claim 16, wherein the upper portion of the upper frame includes a hook-and-loop coupler configured to removably secure an inner liner to the upper frame.

18. The frame assembly of claim 12, wherein the lower frame has a substantially inverted Y-shape such that an upper portion of the lower frame is narrower than a lower portion of the lower frame, wherein the lower portion is bent to form a bowl shape.

* * * * *